United States Patent
Rao et al.

(10) Patent No.: US 7,421,285 B1
(45) Date of Patent: *Sep. 2, 2008

(54) METHOD FOR PROVIDING GASTRONOMIC INFORMATION AND INSTRUCTION WITH AN INTERNET SERVER USING MOBILE COMMUNICATION OR COMPUTING DEVICES AND INTELLIGENT APPLIANCES

(75) Inventors: Raman Kaliputnam Rao, Palo Alto, CA (US); Rekha Kaliputnam Rao, Palo Alto, CA (US); Sunil Kaliputnam Rao, Palo Alto, CA (US); Sanjay Kaliputnam Rao, Palo Alto, CA (US)

(73) Assignee: IP Holdings, Inc., Palo Alto, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 10/871,548

(22) Filed: Jun. 18, 2004

Related U.S. Application Data

(63) Continuation-in-part of application No. 09/281,739, filed on Jun. 4, 1999, now Pat. No. 6,169,789.

(51) Int. Cl.
  *H04B 1/38* (2006.01)
(52) U.S. Cl. .................................... 455/557; 455/556.1
(58) Field of Classification Search ................. 455/557, 455/562.1, 414.1, 466, 556.1; 379/93.12, 379/90.01, 110.01; 705/15, 27
See application file for complete search history.

(56) References Cited

U.S. PATENT DOCUMENTS

| | | | | |
|---|---|---|---|---|
| 5,845,263 | A * | 12/1998 | Camaisa et al. | 705/27 |
| 6,358,546 | B1 * | 3/2002 | Bebiak et al. | 426/232 |
| 6,837,436 | B2 * | 1/2005 | Swartz et al. | 235/472.02 |
| 6,865,261 | B1 * | 3/2005 | Rao et al. | 379/93.12 |

* cited by examiner

*Primary Examiner*—Charles N Appiah
*Assistant Examiner*—Joy K Contee
(74) *Attorney, Agent, or Firm*—Courtney Staniford & Gregory LLP

(57) ABSTRACT

A system for maintaining, tracking, and correlating personal health information with one or more parameters that include gastronomic information, real time ingestion of food, ingestion of medications, ingestion of supplements, adverse allergic reactions, symptoms, health indicators related to the user, recommended procedures, recommended treatment, recommended medications, and notification information for use in an emergency based on user profile. The system includes maintaining the personal health information on the mobile device and a central server. The system further includes maintaining, tracking, monitoring, accessing and correlating personal health information with general medical and gastronomic information from at least one Internet server utilizing the mobile device.

6 Claims, 4 Drawing Sheets

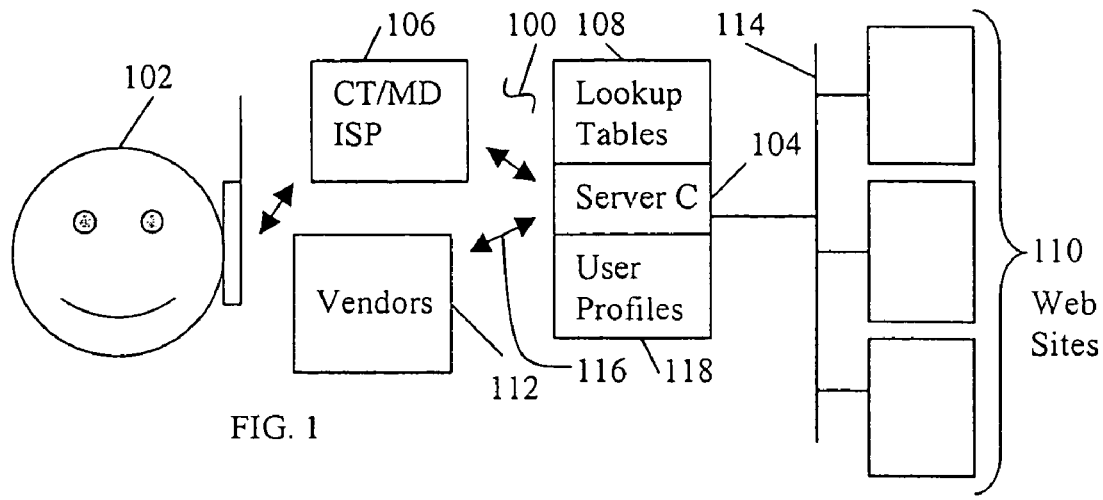
FIG. 1
| Action | Place | Parameter |
|---|---|---|
| Breakfast | Denny's | Time 7AM |
| Lunch | Rudolfo's | 11AM with Jed |
| Dinner | The Place | 7PM with Beth |
FIG. 2
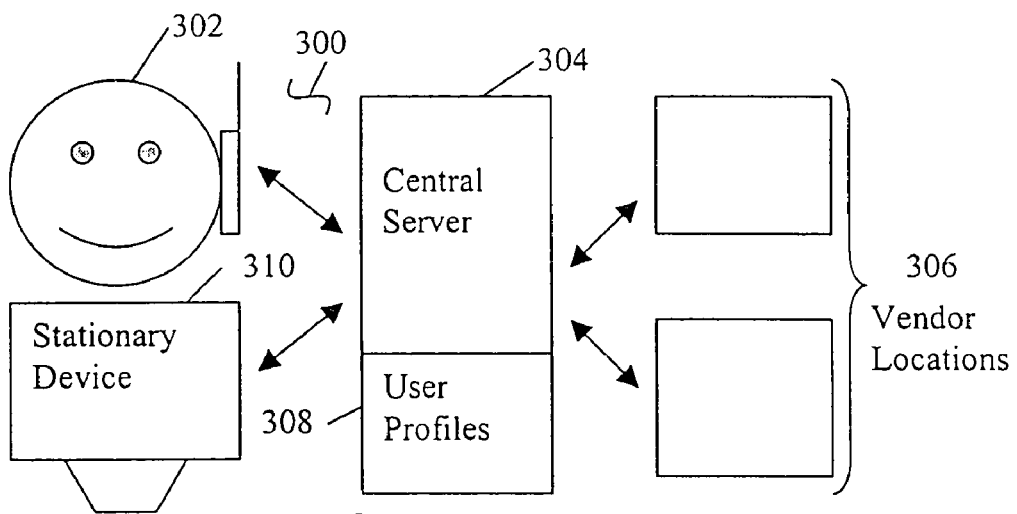
FIG. 3

METHOD FOR PROVIDING GASTRONOMIC INFORMATION AND INSTRUCTION WITH AN INTERNET SERVER USING MOBILE COMMUNICATION OR COMPUTING DEVICES AND INTELLIGENT APPLIANCES

CROSS REFERENCE TO RELATED APPLICATIONS

The present application is a continuation-in-part of application entitled INTELLIGENT KEYBOARD SYSTEM, Ser. No. 09/281,739, filed Jun. 4, 1999 now U.S. Pat. No. 6,169,789.

BACKGROUND OF THE INVENTION

Ingestion of tasty, nutritious food prepared under safe and sanitary conditions is a key factor that affects our daily well being and is an integral part of our attitude and quality of life. However, a sudden desire for food while one is mobile often involves a random search for a vendor, with incomplete information on menu, ingredients used, style of preparation, price, service, quality, health and sanitary conditions and ambiance among numerous other factors that effect our sense of overall satisfaction.

However, especially with respect to impulse dining decisions, comparisons of available sources must be fast, accurate and convenient to have maximum effect. Often available means for making comparisons are not adequate in one or more aspects. Ideally, the user must be able to seamlessly, quickly and conveniently make a fully informed decision that optimizes the users criteria of importance and delivers a value proposition that is satisfying.

Convenient, accurate choices for individual dining are also in the best interest of governments and businesses. Trade and tourism are adversely affected if consumers are uncertain about the taste, quality, safety and price of the local food. While problems with food in strange places are often dismissed as a part of being a "turista", to the extent of dismissing illness as inevitable, the consequences of a mistake in food consumption are often very serious.

Dining comparisons have been handled in an ad hoc manner; such as by chance or relying on advertising which has been forced on the consumer. These methods are inconvenient and annoying, and often provide incomplete or inaccurate information for making a decision. In addition, many dining establishments do not advertise prices, forcing the consumer to guess at the value or quality of the food at that establishment. Since some establishments may charge relatively excessive rates or have unacceptable quality or both, the dining experience may be erratic. It is in the best interest of both a government wishing to encourage trade and tourism and of a consumer desiring to have simple, reliable price comparisons and reasonable quality in a dining experience to have reliable methods for selecting a dining establishment. A consumer needs to know prices, perhaps a history of complaints or commendations, any government actions, especially if they are adverse, and perhaps other things such as reputation for service, or how long one might have to wait for service, and these questions are seldom if ever answered satisfactorily.

Too often, methods for making dining decisions, rather than providing a benefit to the government and consumers, create confusion and uncertainty. This is especially true for cases involving foods in unfamiliar places, for example, where the ingredients may be unfamiliar and safety is perceived as questionable.

SUMMARY OF THE INVENTION

The present invention provides a method for a gastronomic decision and instruction system over wired or wireless means, using an Intelligent Keyboard (IK), a Cellular Telephone (CT) and a mobile Device (MD), a stationary device (SD), a central server and a Multi channel Multiplexing Transmitter and Receiver (MMTR). The system obtains information about food, such as recipes, and food service, which may include safety and other pertinent factors, in real time over a wireless link. The actions include making an inquiry to a trusted central server for the gastronomic information. The inquiry is formatted by the central server for transmission to sources of the information such as vendors, government agencies, consumer protection groups, better business organizations and so forth, or to their web sites. After receiving the information from the sources, the information is displayed, such as on a mobile device. Information about the consumer, such as preferences and concerns, will normally be available locally on the central server, so that information from the sources can be filtered or formatted for the consumer automatically as well as in response to expressed concerns. The present invention includes obtaining gastronomic information from remote sources. This allows the present invention to provide an action such as making a dining reservation at a desired time or obtaining information relating to safety such as food or water quality, or any other need the consumer may have.

Other objects, features and advantages of the present invention will become apparent from the following detailed description when taken in conjunction with the accompanying drawings.

BRIEF DESCRIPTION OF THE EMBODIMENTS OF THE INVENTION

The accompanying drawings, which are incorporated in and form a part of this specification, illustrate embodiments of the invention and, together with the description, serve to explain the principles of the invention:

FIG. 1 shows an embodiment of a gastronomic information system of the present invention.

FIG. 2 shows an embodiment of a gastronomic information system of the present invention in the form of a table of input values for use in a search for a specific gastronomic item, such as a recipe.

FIG. 3 shows an embodiment of a gastronomic information system of the present invention in which a gastronomic transaction is being made with a smart card.

DETAILED DESCRIPTION OF THE PREFERRED EMBODIMENTS

Figure 4:
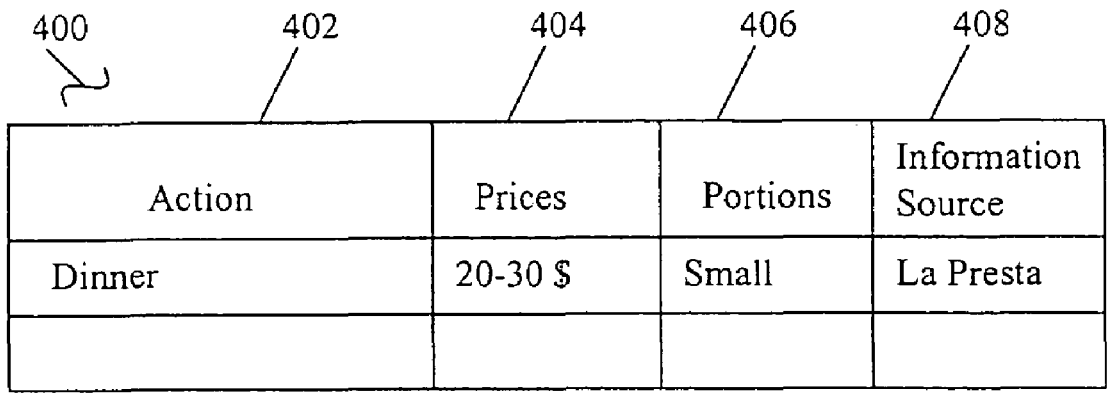
FIG. 4 shows an embodiment of a gastronomic information system of the present invention in the form of an alternate table of input values.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims. For example, the embodiments that follow relate to a wireless unit for making gastronomic decisions, but includes stationary units as well, such as personal computers (PCs). Further, the gastronomic inquiry or request can be in any form of intelligence, such as key entries from a keyboard, voice in any language, graphics such as a key click on a graphic page, mouse clicks on a view, or even tactile responses or depressions of a foot pedal. Required translations, such as from one language to another or from a tactile entry to a voice command, are made automatically.

The present invention is a gastronomic inquiry system with a display device for making a gastronomic inquiry to an information server having a gastronomic database. The present invention includes displaying a response to the gastronomic inquiry from the information server on the display device. The present invention also includes sending the gastronomic inquiry from the display device to the information server, preparing a gastronomic response to the gastronomic inquiry on the information server, and receiving the gastronomic response to the gastronomic inquiry from the information server with the display device. A preferred embodiment includes formatting the gastronomic response to the gastronomic inquiry on the display device, and displaying the formatted gastronomic response to the gastronomic inquiry on the display device.

In the present invention a user desiring to make a comparison or request an action relating to a comparison uses a mobile device, such as a cell phone for making a wireless call, to a central server of the present invention. The central server receives the request for the action, and parses the necessary information to service the call. Any information may be parsed, but will normally include identification (ID) of the user, information about the language, the basis or type of the action, the number of actions desired, and any parameters that may be pertinent. The parameters involved may include, for example, inputting a limit on the values for a comparison, such as not more than a certain amount in US dollars. In another example of a parameter, an action might depend on a certain type of food being available before a transaction will be authorized.

A preferred embodiment of the invention includes a method for making a gastronomic inquiry with a display device to an information server having a gastronomic database. A mobile device such as a cellular telephone is used for displaying a response to the gastronomic inquiry from the information server on the display device. The preferred embodiment includes sending the gastronomic inquiry from the display device to the information server. The preferred embodiment also includes preparing a response to the gastronomic inquiry on the information server. The mobile device is used for receiving the response to the gastronomic inquiry from the information server with the display device. The preferred embodiment includes formatting the response to the gastronomic inquiry on the display device, and displaying the formatted response to the gastronomic inquiry on the display device.

FIG. 1 shows an embodiment of a gastronomic decision system 100 of the present invention. In FIG. 1, a user with a cellular telephone/mobile device CT/MD 102 communicates with a central server 104 through, for example, wireless service provider for the CT/MD (ISP) 106. Server 104 uses, for example, lookup tables 108 and user profiles 118 to set an environment for the specific action. The environment set might include the ID of the user, the language being used, the type of action, and the value expected from a transaction, along with flags for any limits desired by the user. With the environment set, the central server obtains the desired information, such as recipes or dining information from web sites 110 of vendors over the internet 114 or directly from the vendors 112, such as by automatic email 116. The information gathered is then inserted into the environment set up for the consumer, and further processed, such as by converting to the language of the consumer or adjusting a format as desired by the consumer. Depending on the results obtained and the urgency, the user is notified by phone, email, or other means.

FIG. 2 shows an embodiment of the gastronomic decision system of the present invention showing how a table 200 of values might be used to identify the source and value of actions being inquired about or required by the consumer. In FIG. 2, a template for the table 200 has been created, either from the central server or from software, such as in the mobile device being used for inputting a request for an action 202. As shown, the template allows entry of a requirement, such as a place 204 for the action, and also allows entry of parameters 206. As an example, an ethnic food preference might be input along with a preferred time. This could be also be a serving size such as a weight in grams or ounces rather than a time, and might be identified as a basis for a price comparison. While the table shows only two items in response to the action, place and time, it will be understood that any number of items could be involved.

FIG. 3 shows an embodiment of the gastronomic decision system 300 of the present invention. In FIG. 3 a user with a mobile device (MD) 302, which could also be a stationary device (SD) 310 as shown, communicates a price comparison request or a request for a recipe or other information to a central server 304. As described above, the central server 304, such as by using user profiles 308, sets a consumer environment, such as the consumer ID, language being used, food ethnicity desired, or other parameters, such as weight, seasoning, and service rating. Answers will be sent back to the mobile device or by email or otherwise, as indicated by the mode of communication set up by the environment. The central server interrogates vendor locations 306 for the information desired. Locations 306 respond with the desired information, or with some other information, such as a location with more current or pertinent information. The central server 304 processes the information received from the locations 306, such as by parsing the information to determine the language used, and determines how to communicate the information to the user, such as to MD 302. If new information relating to the user has been developed in the environment, it will be used to update the user profile in the user profiles 308.

FIG. 4 shows an embodiment of a gastronomic decision system of the present invention with table 400, an alternative version of the table 200 of FIG. 2. In FIG. 4, a template for building table 400 allows data to be assembled in response to an action 402, prices 404, portions 406 and information source 408, such as the name of a vendor supplying a price.

Figure 5:
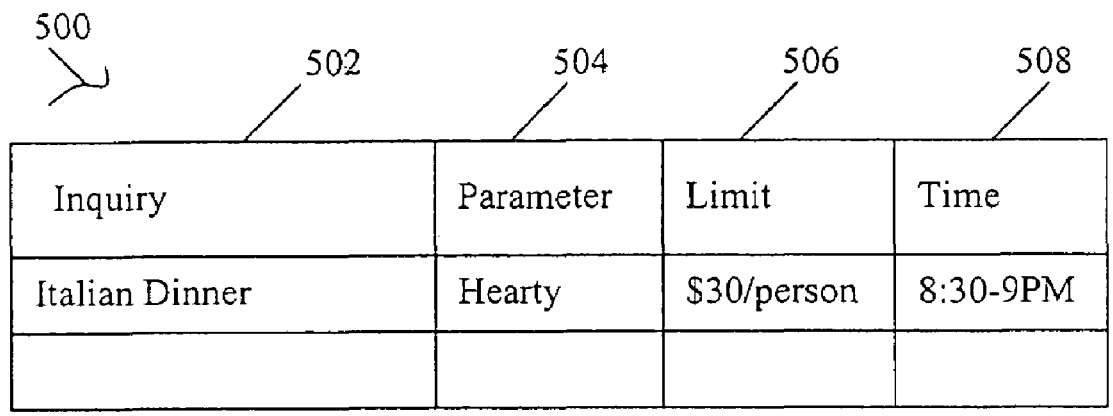
FIG. 5 shows an embodiment of a gastronomic information system of the present invention in the form of another table of input values.

FIG. 5 shows another embodiment of the gastronomic decision system of the present invention with a table 500 for entry of information, such as a menu or a recipe. Table 5 relates to an inquiry 502. Table 500 also allows the entry of a parameter 504 such as a portion size, and another parameter 506; such as a limit above which (or below which) an action is not desired or is not to be completed. There is also an entry such as a time 508 at which the action is to be completed, such as when it is desired to dine at a desired location.

Figure 6:
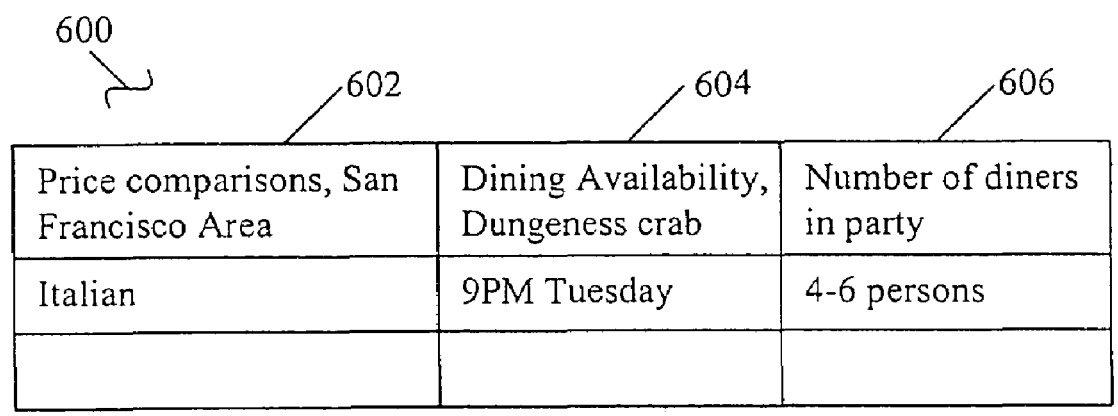
FIG. 6 shows an embodiment of a gastronomic information system of the present invention illustrating a table of values representing responses from sources of gastronomic information to requests for information such as in FIGS. 2, 4 and 5.

FIG. 6 shows another embodiment of the gastronomic decision system of the present invention showing a table 600. In FIG. 6, table 600 allows, for example, entries for the type of comparison 602, the gastronomic item to be compared 604, and the number of diners 606. Clearly, as shown in FIG. 2 and again in FIG. 4, the entries in table 600 could be expanded to include other desired information, such as the date and time at which dining is desired, and so on.

Figure 7:
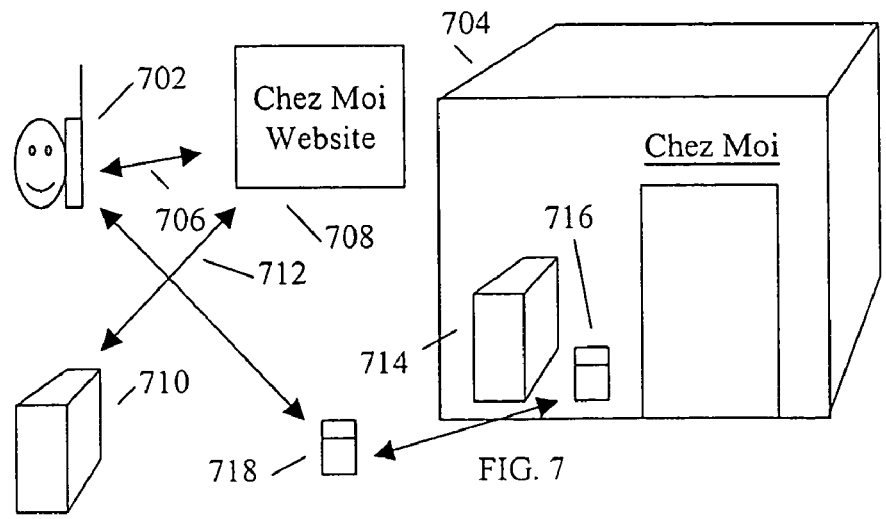
FIG. 7 is an embodiment of the present invention illustrating an intelligent scheduler.

FIG. 7 is an embodiment of the present invention illustrating an intelligent scheduler 700. In FIG. 7, the IK/CT/MD/SD 702 may be used to make reservations at a dining establishment 704 and have the reservations queued or prioritized and services staged for optimal delivery and user satisfaction. A connection 706 is made by wired or wireless means to the web site 708 of the restaurant 704. The software resident on a network server 710 located on the Internet 712 or a local server 714 located, for example, at the restaurant 704 recognizes the caller ID or telephone number. The server 712, 714 may then cross reference to a name and picture of the person. This enables the server 712, 714 to look up the profile of customer and determine preferences such as seating, type of food, favorite chef, favorite menu items, preferred times and taste. It enables the use of specific preparation methods, safe preparation methods to avoid allergic reactions if required, favorite waiter, type of wine, time of arrival, and typical or intended duration of stay among numerous other factors. The user may login and set his preference profile on the server with reference to almost any number of factors. The software resident on an Internet server 714 or a local server 712 allows looking up the data from the database and customizing the dining experience seamlessly. An MMTR 716 may be in the local loop at the restaurant 704 or connect via a Wireless Service Provider (WSP) 718. Both options are independently possible or may coexist.

Figure 8:
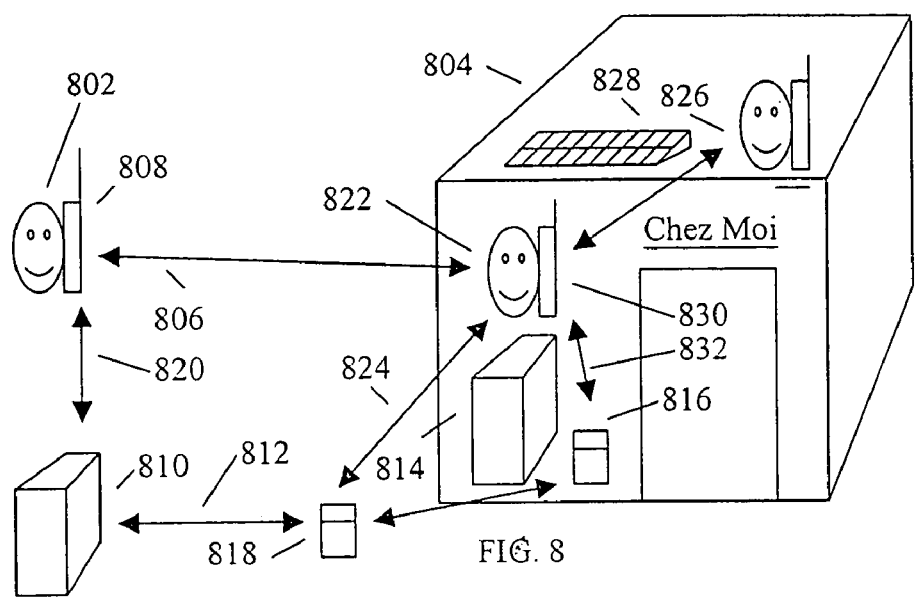
FIG. 8 shows a preferred embodiment of the invention with a dining network.

FIG. 8 shows a preferred embodiment of the invention with a dining network 800. In FIG. 8, the restaurant 804 has an MMTR 816 and the use of a local server 814 and an Internet server 810 on the Internet 812 on which the database and software reside. The customer 802 with a mobile device may be on one channel in the wired or wireless local loop 806 while being on voice or data on other channels such as data channel 820. Similarly, the restaurant staff that carry mobile devices such as waiter 822 may also be in one or more local channels such as local channel 832 and one or more outside channels such as outside channel 824 either through the MMTR 816 or the WSP 818. The waiter 822 may instruct the chef 826 by wired or wireless means and have the complete profile or a selected profile relating to the food preparation and menu made available to the chef 826 for customized preparation. The chef 826 may access the data by wired or wireless means. In addition the customer 802 may by wired or wireless means such as wireless connection 820 using a mobile Cellular Telephone/Mobile Device (CT/MD) 808, which could also be a stationary device, instruct and follow the progress of his order and preparation. The CT/MD 808 may be in local loop 806 under the control of an MMTR 816 or may use the WSP 818.

The billing may be done by the waiter using an Intelligent Keyboard (IK) 828 or by the customer 802 using a CT/MD 808 and have the transaction seamlessly recorded for debiting/crediting to respective accounts. Customer 802 may fill in memo features such as who attended the dinner, the food and wine charges separately, and have the appropriate expense report filled in seamlessly and even sent to a company in case it is a business expense.

Greeting the customer: upon arrival the customer is greeted by name, as the photograph of the customer is available to any waiters such as the hostess with a complete profile also accessible. An image of the customer 802 may be acquired by the hostess or automatically at the entry point of the restaurant 804 on a real time basis and instantaneously compared to the database to provide name and other information for greeting and seating. The waiter 822 is also now made aware of the user identity by having the data available on a mobile device 830 that he carries.

The menu items, recipes, their complete ingredients and preparation technique are accessible by the customer 802 using the CT/MD 808 which may access the restaurant 804 database located on a local server 810 or an Internet server 814. The access may be through a WSP 818 or the local loop 806 via the MMTR 816. The customer 802 may choose the items desired or instruct the chef 828 to prepare items in a prescribed manner.

Anaphylaxis is an allergic reaction to certain types of foods. An estimated 1 to 2 percent of the population risks anaphylaxis from foods. There are warning signs when exposed for the first time but subsequent attacks may be deadly. This food allergy poses serious health hazards for the customer 802 and a potential legal liability to the restaurant 804. Knowing the allergic reaction profile and having this data linked to a database is important. The customer 802 may input such as via the CT/MD 808 his health and allergic reaction profile. These factors are often deadly and pose serious liability issues. The restaurant 804 may thus customize the food preparation by providing customer 802 specific instructions to the chef 828 by wired or wireless means through the MMTR 816 local loop or the WSP 818. The database of customer 802 profile, health and allergy factors, emergency contacts and other information is also available on local server 810 or Internet server 812. Emergency notification may be set automatically. The customer 802 may seamlessly track the factors that affect his health, weight, caloric intake and fitness by having the ingested food details tracked on a database. The inputs may be by the user 802 on a Cellular Telephone/Mobile Device/Stationary Device (CT/MD/SD) 808 or may be auto entered and tracked by what was ordered in a restaurant 804. Alternately, the customer 802 database may be accessed on the CT/MD/SD 808 to advise the customer 802 about ordering. The CT/MD/SD 808 can also advise on limiting certain menu items based on tracking daily, weekly and monthly caloric intake and factors such as body mass index, BMI—an obesity indicator—and other health and fitness management indices. These indices may be preset by the customer 802 and tracked using, for example, the CT/MD 808. The BMI and other indices may be displayed on the CT/MD 808. In addition the software resident on the local server 810 or an Internet server 814 or a database may track the exercise done daily and advise that additional work out is needed because of specific type or quantity of food ingested in a given period.

Figure 9:
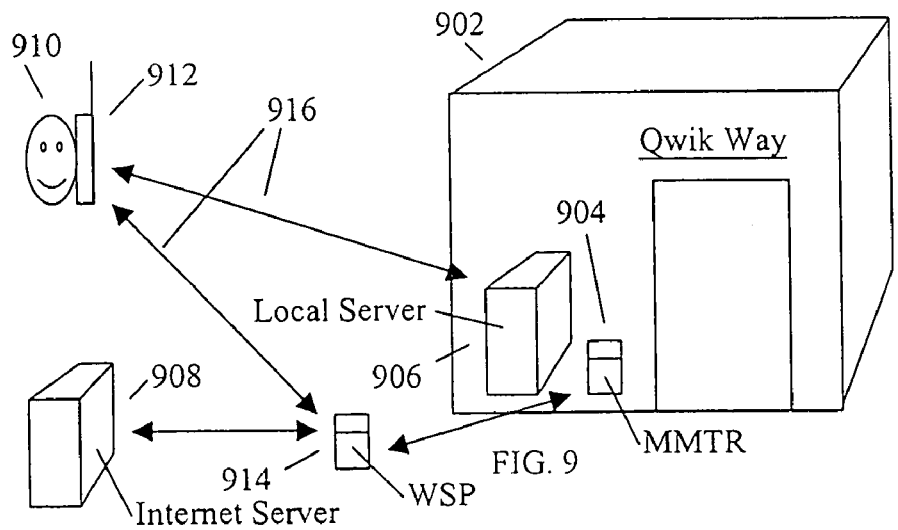
FIG. 9 is an embodiment of the present invention illustrating an interface with a fast food restaurant.

FIG. 9 is an embodiment of the present invention illustrating an interface 900 with a fast food restaurant 902. In FIG. 9, a fast food or other establishment 902 has a MMTR 904, a local server 906 and a connection with an Internet server 908. As the customer 910 is on, for example, the highway he may access the Internet server 908 with a mobile device 912 via a WSP 914. This information through the MMTR 904 may be passed on to the local server 906 for action. A customer 910 in the restaurant 902 may access one or more channels of the restaurant 902 MMTR 904 and be connected to the server 906, 908 and his order processed. The MMTR 904 plays a key role in establishing capabilities as described in the present invention. In addition an embedded MMTR-like function in each CT/MD 912 allows the customer 910 to simultaneously communicate on one or more channels 916.

Figure 10:
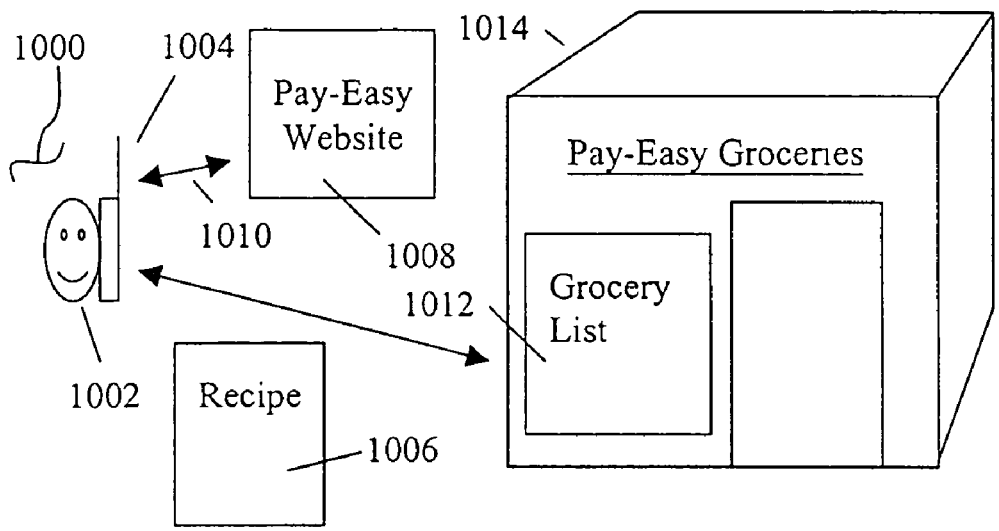
FIG. 10 is an embodiment of the present invention showing an interface for recipes and grocery lists.

FIG. 10 is an embodiment of the present invention showing an interface 1000 for recipes and grocery lists. In FIG. 10, the customer 1002 while in stationary or mobile mode may access via a CT/MD/SD 1004 various recipes 1006 from a website 1010 located on the Internet 1010 which could also be a local server. These recipes 1006 may be viewed on the CT/MD/SD 1004 and selections made. These selections may automatically generate a grocery list 1012 that may be sent to a online or offline grocer 1014 for delivery or pickup.

Figure 11:
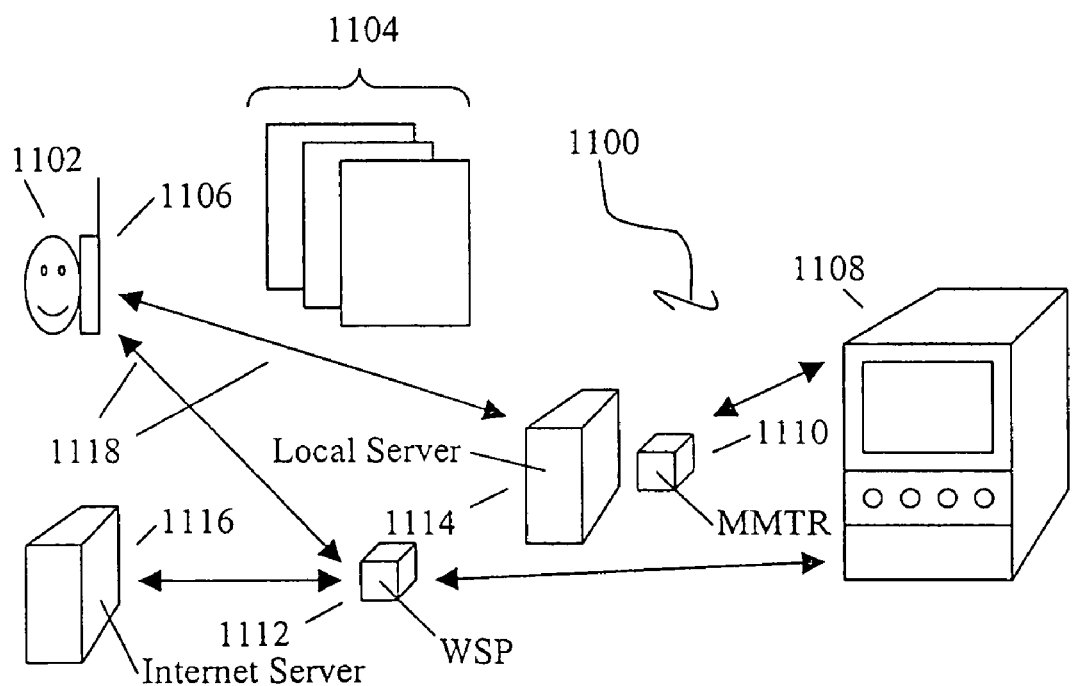
FIG. 11 is an embodiment of the present invention illustrating an interface for supplying recipes to an intelligent cooking appliance.

FIG. 11 is an embodiment of the present invention illustrating an interface 1100 for supplying recipes 1104 to an intelligent cooking appliance 1108. In FIG. 11, the customer 1102 sends a selection of recipes 1104 by wired or wireless means 1118 via a CT/MD/SD 1106 to an intelligent cooking appliance 1108. The appliance 1108 may be in the local loop via an MMTR 1110 or may receive input via a WSP 1112. The software resident on the local server 1114 or the network server 1116 enables the selected recipes 1104 to be prepared by an intelligent appliance 1108 or otherwise cooked and be staged for serving. In addition to instructing the intelligent appliance 1108, a Cellular Telephone/Mobile Device/Stationary Device (CT/MD/SD) 1106 may be used to monitor the progress and performance of the intelligent food preparation appliance 1108. The user 1102 may view recipes 1104 or menus 1104 in one or more languages using the CT/MD/SD 1106 and order or instruct in one or more languages using language translation software resident on a local server 1114 or an Internet server 1116.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A system comprising:

a mobile device;

a central server; and a customer profile coupled to the mobile device and the central server and comprising data of a user selected from a group consisting of ingestion of food, ingestion of medication, ingestion of supplements, ailments, adverse allergic reactions, symptoms, gastronomic indicators, health indicators related to the user, recommended procedures, recommended treatment, recommended medications, and notification information for use in an emergency, wherein one or more of the mobile device and the central server is configured for acquiring and correlating data related to one or more of ingestion of food, medication, and-supplements with data of the customer profile, wherein the mobile device is configured to output, in response to the correlating, monitoring and control information relating to the ingestion of food, medications, and supplements.

2. A system comprising:

a mobile device including a processor coupled to a gastronomic component, the gastronomic component configured to generate a request for a first set of gastronomic data; and a server coupled to the mobile device and coupled to a plurality of sources of gastronomic data, the server configured to retrieve a second set of gastronomic data from at least one of the plurality of sources in response to the request, wherein the second set of gastronomic data includes data relating to a profile of the user, the server configured to generate the first set of gastronomic data from at least a portion of data of the second set using the profile, the server configured to transfer the first set of gastronomic data to the mobile device for display.

3. The system of claim 2, wherein the profile includes data of one or more of preferred foods, food costs, food allergies, medications, supplements, medical personnel, and medical procedures, wherein a data type of the data includes one or more of audio, video, photographic, and text.

4. The system of claim 2, wherein the second set of gastronomic data includes data of one or more of food, recipes, food services, food preparation, beverages, dining facilities, food costs, and menus.

5. The system of claim 2, wherein the server is configured to generate the first set of gastronomic data by parsing the second set of gastronomic data using the profile of the user.

6. The system of claim 2, wherein one or more of the mobile device and the server are configured to generate gastronomic instructions using the profile and the first set of gastronomic data, wherein the gastronomic instructions include one or more of health maintenance instructions, health management instructions, and personal safety instructions, wherein the mobile device is configured to display the gastronomic instructions.

* * * * *